United States Patent [19]

Ferrari et al.

[11] Patent Number: 5,728,164
[45] Date of Patent: Mar. 17, 1998

[54] HIP JOINT FOR ORTHOPEDIC ORTHESIS

[75] Inventors: Adriano Ferrari, Reggio Emilia; Mauro Messori, Bologna; Marco Lusvardi, Capri; Gianpaolo Varroni; Luca Piancastelli, both of Bologna, all of Italy

[73] Assignee: Officine Ortopediche Rizzoli S.p.A., Bologna, Italy

[21] Appl. No.: 533,414

[22] Filed: Sep. 25, 1995

[30] Foreign Application Priority Data

Sep. 29, 1994 [IT] Italy .................. B094A0427

[51] Int. Cl.⁶ .................................... A61F 5/00
[52] U.S. Cl. .................... 623/31; 602/16; 602/19; 602/23
[58] Field of Search ............... 623/30, 31, 39, 623/44; 602/5, 10, 16, 19, 23, 36

[56] References Cited

U.S. PATENT DOCUMENTS

| | | | |
|---|---|---|---|
| 2,578,108 | 8/1951 | Thornton | 602/16 |
| 3,449,769 | 6/1969 | Mizen . | |
| 4,620,532 | 11/1986 | Housworth | 602/16 |
| 4,697,808 | 10/1987 | Larson | 623/30 |
| 4,738,252 | 4/1988 | Friddle et al. | 602/16 |
| 4,969,452 | 11/1990 | Petrofsky et al. | 623/31 |
| 5,320,590 | 6/1994 | Poplawski | 602/5 |
| 5,476,441 | 12/1995 | Durfee et al. | 602/23 |

FOREIGN PATENT DOCUMENTS

| | | |
|---|---|---|
| 3219649 | 12/1983 | Germany . |
| 1188647 | 4/1970 | United Kingdom ............ 623/30 |
| 2206494 | 1/1989 | United Kingdom . |
| 9216177 | 10/1922 | WIPO . |

*Primary Examiner*—John G. Weiss
*Assistant Examiner*—Bruce E. Snow
*Attorney, Agent, or Firm*—Guido Modiano; Albert Josif

[57] ABSTRACT

A hip joint for orthopedic orthesis comprising a pelvic attachment to which the tops of two arms are articulated, and in which the arms are adapted to be rigidly coupled to the top of respective thigh-leg-foot braces and are provided with respective hip locking devices that can be disengaged manually to allow the patient to sit; two bushes having substantially vertical axes are fixed laterally to the pelvic attachment and two shafts are articulated to the bushes; the arms are articulated to the shafts in a downward region about substantially horizontal axes; the arms are provided with elements for kinematic connection to the bushes, so that each torsion of the shaft with respect to the bush is matched by a rotation of the arm with respect to the shaft; and the arms are connected by motion transmission elements adapted to complementarily transmit the rotation-torsion movements from one arm to the other.

5 Claims, 6 Drawing Sheets

HIP JOINT FOR ORTHOPEDIC ORTHESIS

BACKGROUND OF THE INVENTION

The present invention relates to a hip joint for orthopedic orthesis for coordinating the movements of the legs of disabled people.

Dynamic ortheses aiming at controlling and reproducing some of the natural movements of the legs by acting mechanically from outside the body have been devised to allow paraplegics who have lost muscle activity of the legs to walk.

Ortheses have been devised in this particular field which are used together with a walker or with two antebrachial crutches and are substantially constituted by a pelvic attachment connected, on each side, to a hip joint having only one degree of freedom and a horizontal rotation axis: the joints have respective arms that are rigidly coupled, in their lower region, to the top of respective braces supporting the thigh, the leg, and the foot. The arms are furthermore connected one another by means of sheathed control cables (cables that are longitudinally slideable in respective sheaths as for example a Bowden Cable) associated with corresponding lever systems adapted to transmit the mutual relative angular movements of the limbs, so that the flexion of one arm is matched by the extension of the other arm.

These cables also allow some posture control: the cable lying at the rear, with respect to the axis of the mechanical articulation, in fact limits excessive flexion of the trunk on the thighs, whereas the cable lying in front of the axis of the mechanical articulation contrasts excessive extension of the trunk with respect to the thighs: the ability of the individual to keep his balance in an upright posture, even without resorting to orthopedic supports for the arms, is thus increased.

When the patient wishes to sit, he disengages the hip joints, which are conveniently provided with a manually actuatable locking device.

Braces of the above-mentioned type (known as RGO, which is an acronym of Reciprocating Gait Orthosis) entail, for the patient, a gait that is inevitably very rigid and unnatural, since it is in fact limited to a series of flexions and extensions of the legs that resemble a parade step, which is not very advantageous in terms of locomotion.

It is known that in the gait of healthy individuals, the hip of the swinging side, which at the beginning of suspension is in a rearward position with respect to the pelvis, at the end of suspension is further forward than the contralateral one; that is to say, the hip rotates on a horizontal plane about the supporting limb over an articulation angle that can range from 5 to 15 degrees.

When the leg that is about to start suspension is lifted off the ground, it is turned inwardly with respect to the pelvis, whereas at the instant of contact, which ends the suspension phase, it is turned outwardly with respect to the pelvis.

Accordingly, ortheses have been provided in which the hip joints, in addition to being provided with a horizontal rotation axis, also have appropriate articulations that allow them to rotate about an axis lying longitudinally with respect to the leg (this rotation about an axis that is substantially longitudinal with respect to the leg or is vertical is termed "torsion" hereinafter). In this case, too, the articulations are interconnected by means of sheathed cables, so that the rotation and torsion of one arm in certain directions causes the rotation and torsion of the other arm in opposite directions: joints of this type, however, have the drawback that the torsion and rotation motions of the arms are transmitted independently of each other, and therefore the balance of the patient can be unsteady; moreover, the presence of numerous sheathed cables entails considerable difficulties in adjustment and tuning.

SUMMARY OF THE INVENTION

A principal aim of the present invention is to obviate the above-mentioned drawbacks of conventional devices by providing a hip joint for orthopedic orthesis for coordinating the movements of the legs that allows a more natural gait, allows to make longer half-steps, as well as a better postural alignment during walking and causes less fatigue to the patient.

An object of the present invention is to provide a hip joint whereby the overall stability of the patient is increased by means of postural compensations not only along the sagittal plane (flexion-extension) but also along the horizontal plane (rotation of the pelvis with respect to the supporting base): the arms particularly benefit from this, since they are less engaged in support activities and are therefore more available for praxis.

Within the scope of this aim, another object of the present invention is to achieve the above aim with a structure that is simple, relatively easy to manufacture, safe in use, effective in operation, and of relatively low cost.

This aim and these objects are achieved by an orthopedic orthesis according to the appended claims.

BRIEF DESCRIPTION OF THE DRAWINGS

Further characteristics and advantages will become apparent from the following detailed description of a preferred but not exclusive embodiment of a hip joint for orthopedic orthesis according to the invention, illustrated only by way of non-limitative example in the accompanying drawings, wherein.

DESCRIPTION OF THE PREFERRED EMBODIMENTS

Figure 1A:
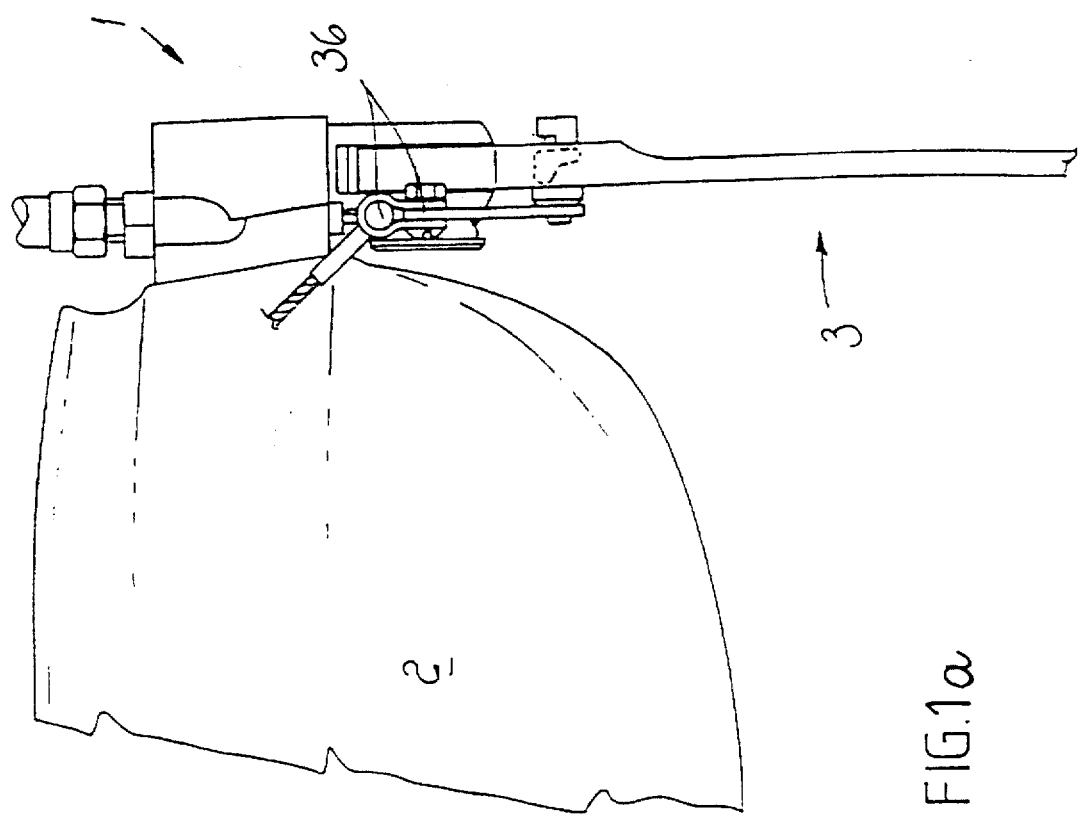
FIG. 1a is a view of the orthopedic orthesis of FIG. 1 as attached to the pelvis of the patient.
Figure 1:
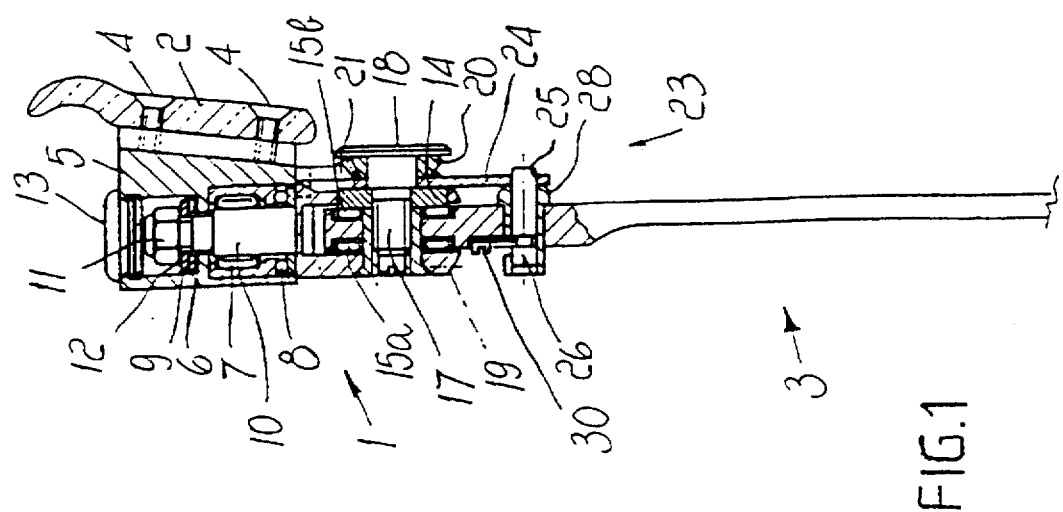
FIG. 1 is a partially sectional cutout rear view of an orthopedic orthesis equipped with hip joints according to the invention.
Figure 2:
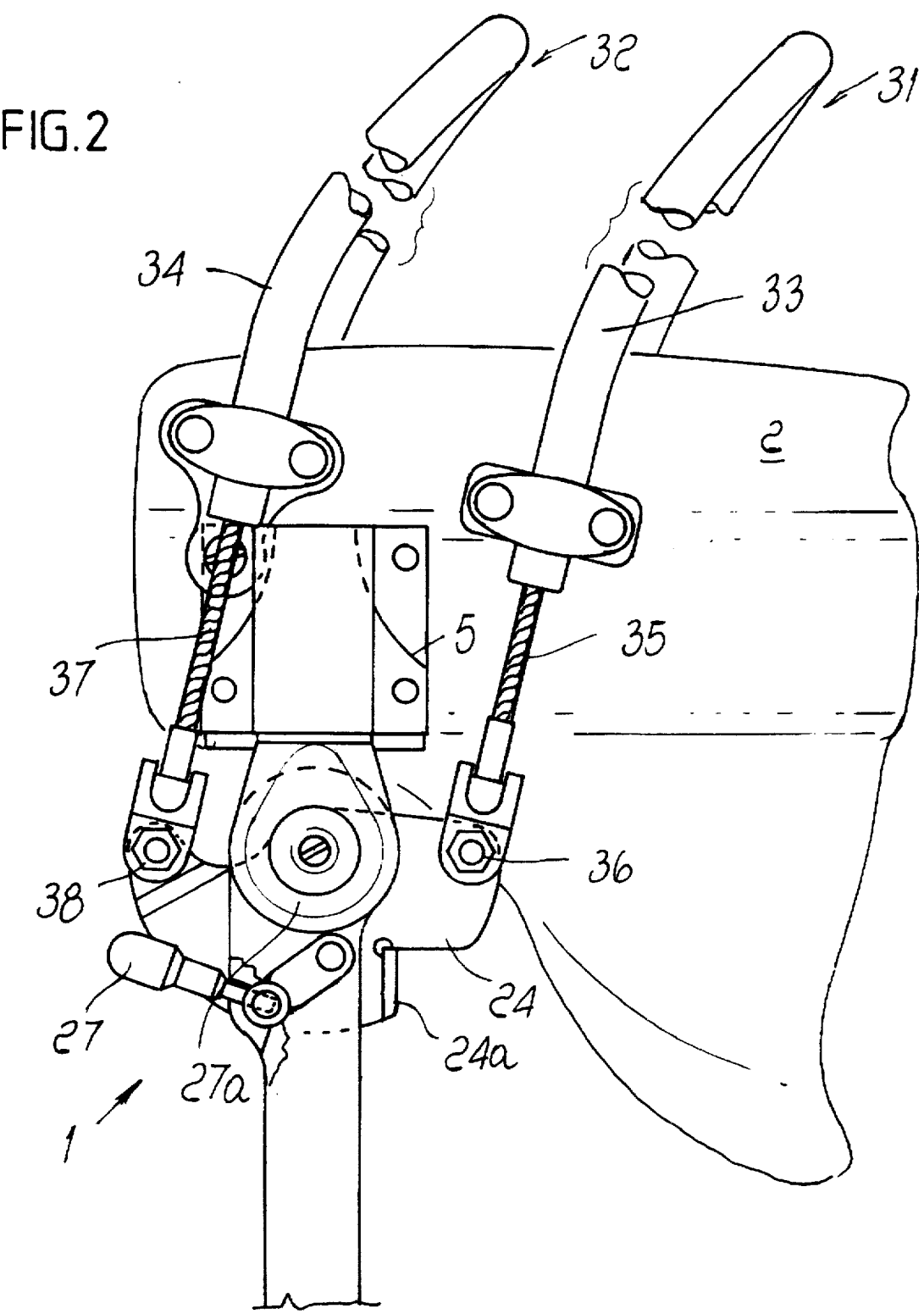
FIG. 2 is an enlarged-scale side view of one of the joints of FIG. 1.
Figure 3:
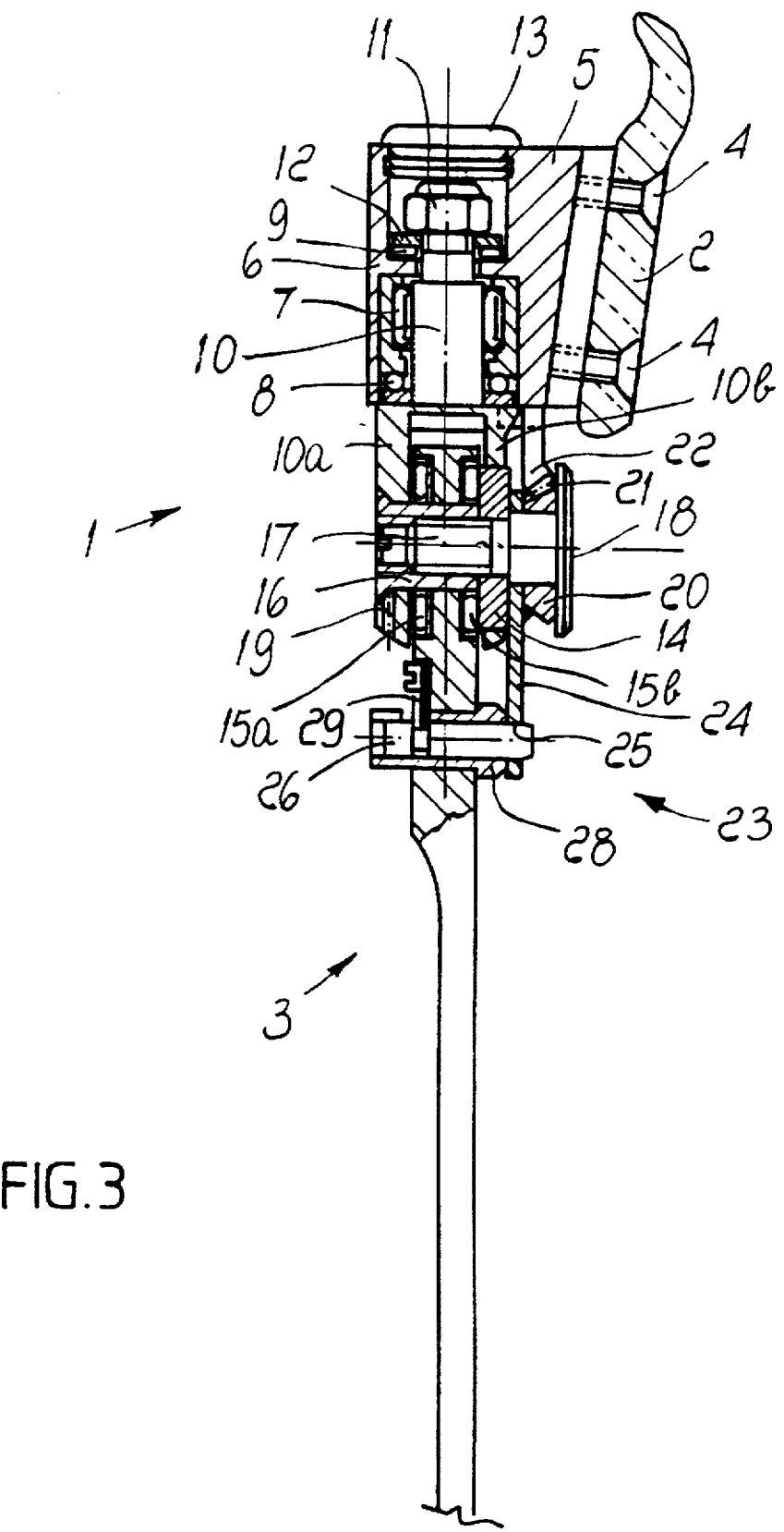
FIG. 3 is an enlarged-scale rear view of the joint.

With reference to the above figures, the reference numeral 1 generally designates the hip joint for orthopedic orthesis according to the invention.

The orthesis comprises a pelvic attachment 2 that is rigidly coupled to the pelvis of the patient and to which the tops of two lateral arms 3 are symmetrically articulated; said arms are rigidly coupled to two braces for containing and fixing the patient's legs.

Two plates 5 are fixed, by means of bolts 4, on either sides of the pelvic attachment 2 and are rigidly coupled to respective bushings 6 having substantially vertical axes: two shafts 10 are mounted in the bushings 6 so that they are rotatable by means of roller bearings 7 and 9 and ball bearing 8 said shafts are locked to the bushings at the top by means of a nut 11 and a washer 12, and the top of the bushings is closed with a cap 13 made of a material such as plastics.

In the following, reference will be made to the left and right joints so that the component elements may be referred to with plural since each element of the left joint has a corresponding element for the right joint.

The lower ends of the shafts 10 are fork-shaped, with tines 10a and 10b, for coupling to the top of the arms 3: coupling is obtained by means of two cylindrical roller bearings 15a, 15b, which are recessed within corresponding seats of the tops of the arms; by means of a washer 14, which is centered in a corresponding hole of the tine 10b of the fork; and by means of a bushing 16, which has a frustum-shaped tip, is centered in a corresponding hole of the other tine 10a of the fork, and is crossed by a threaded axial hole in which the shaped pivot 17, ending with the flat head 18, is screwed.

The bushing 16 is anchored to the fork 14 by means of a radial grub screw 19; a sprocket 20 is mounted on the pivot 17 so as to rest against the head 18 and has a 45° set of teeth that meshes with some teeth of a fixed toothed profile 21, which has a 45° set of teeth and is formed at the lower end of an L-shaped element 22 that is fixed to the plate 5 by means of bolts; the axis of the sprocket 20 coincides with the axis of the pivot 17, whereas the axis of the fixed toothed profile coincides with the axis of the bushing 6: the axes of the bushing 6 and of the pivot 17 are substantially concurrent and mutually perpendicular.

The reference numeral 23 generally designates a hip locking device that can be disengaged manually to allow the patient to assume the sitting posture: the toothed sprocket 20 is welded to a flat element 24 centered on the pivot 17; the flat element 24 has a through hole 25 for the snap-together insertion of a pin 26 provided with a radial trigger 27; the pin is slideably mounted in a transverse guide 28 of the arm and is pushed in the direction for entering the hole 25 by an elastic lamina 29 fixed to the arm 3 by means of a screw 30: by acting on the trigger 27 it is possible to make the pin 26 enter the hole 25 or disengage it in order to rigidly couple the flat element to the arm during walking, or respectively to disengage them: actuation of the trigger is facilitated by a cam profile 27a formed on the front face of the arm; the flat element 24 has a shaped lug 24a that is folded so as to be L-shaped and is adapted to act as a stroke limiter for the backward rotation of the corresponding arm and to assist the action of the pin.

The toothed sprockets 20, which are rigidly coupled to the arms by the pins 26, and the fixed toothed profiles 21 constitute means for the kinematic connection of the bushings to the arms so that each torsion of the one of the shafts with respect to the respective bushings is matched by a rotation of the arm with respect to the shaft: the transmission ratio between the sprocket and the toothed profile provided for the particular case shown in the figure is 2:3, so that the torsion angle is two thirds of the flexion angle, but it is possible for it to assume other values as well.

The right and left arms 3 are connected by motion transmission elements adapted to complementarily transmit the rotation-torsion movements from one arm to the other.

The motion transmission elements are constituted by sheathed cables 31 and 32, in which the ends of the sheaths 33 and 34 are rigidly coupled to the two sides of the trunk; the end of the first sliding cable 35 is coupled to holes 36 of the eccentric flat elements lying to the rear of the articulations of the arms and the end of the second sliding cable 37 is coupled to eccentric holes 38 lying in front of the articulations of the arms.

Figure 4A:
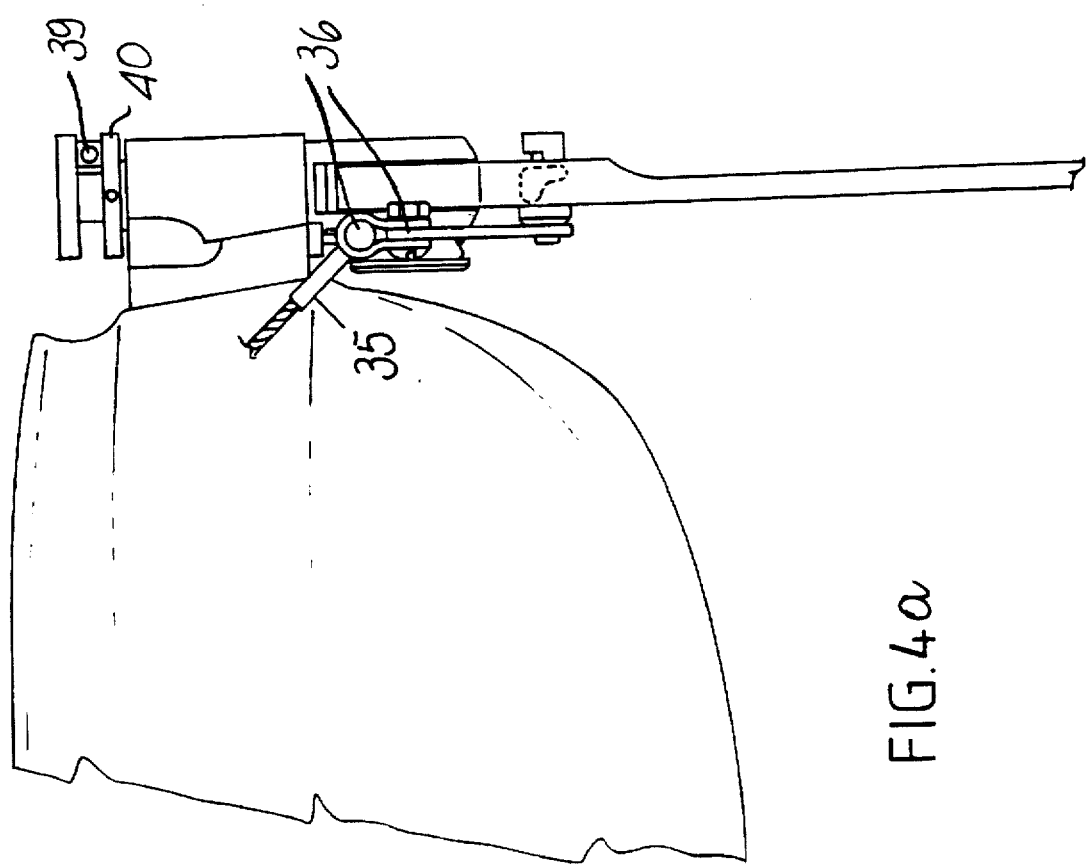
FIG. 4a is a view of the orthopedic orthesis of FIG. 4 as attached to the pelvis of the patient.
Figure 4:
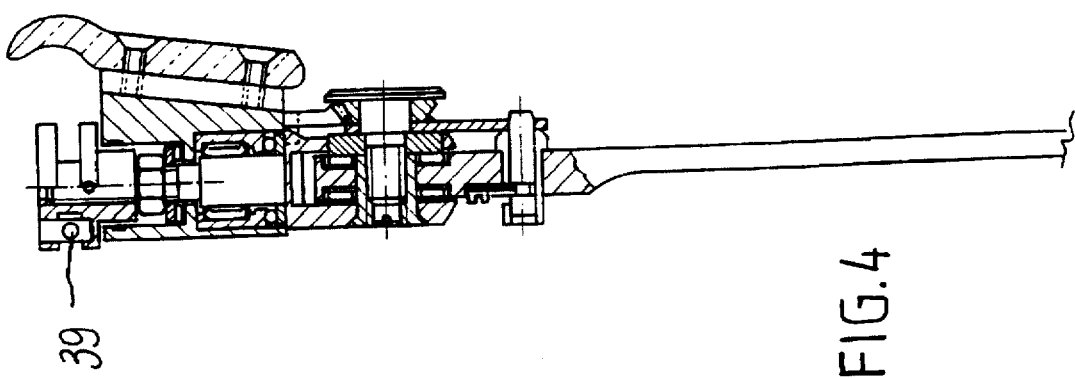
FIG. 4 is a partially sectional cutout rear view of an orthopedic orthesis equipped with an alternative embodiment of the joint.
Figure 7:
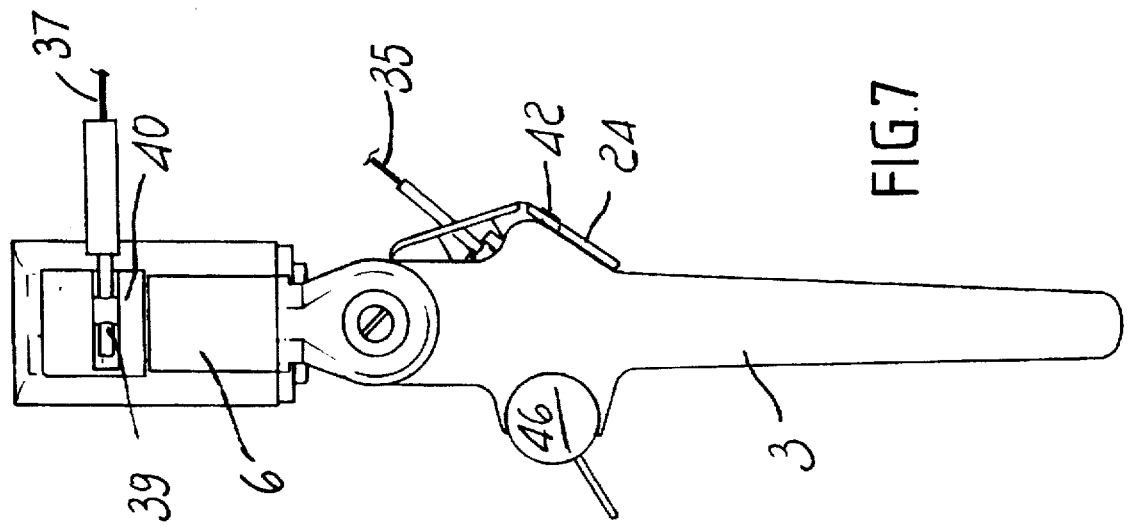
FIG. 7 is a front view of the joint, from the outside, in a preferred embodiment that is a combination of those shown in FIGS. 4 and 5.

In another embodiment (FIGS. 4 and 4a), the ends of the second cable 37 are coupled to eccentric elements 39 of disks 40 fixed to the shafts 10 in an upward region in the manner shown in FIG. 7.

Instead of the two sheathed cables 31 and 32 of the type capable of transmitting only traction forces through the sliding cables, it is possible to use a single sheathed cable of the type that can also transmit thrusting forces.

Figure 5:
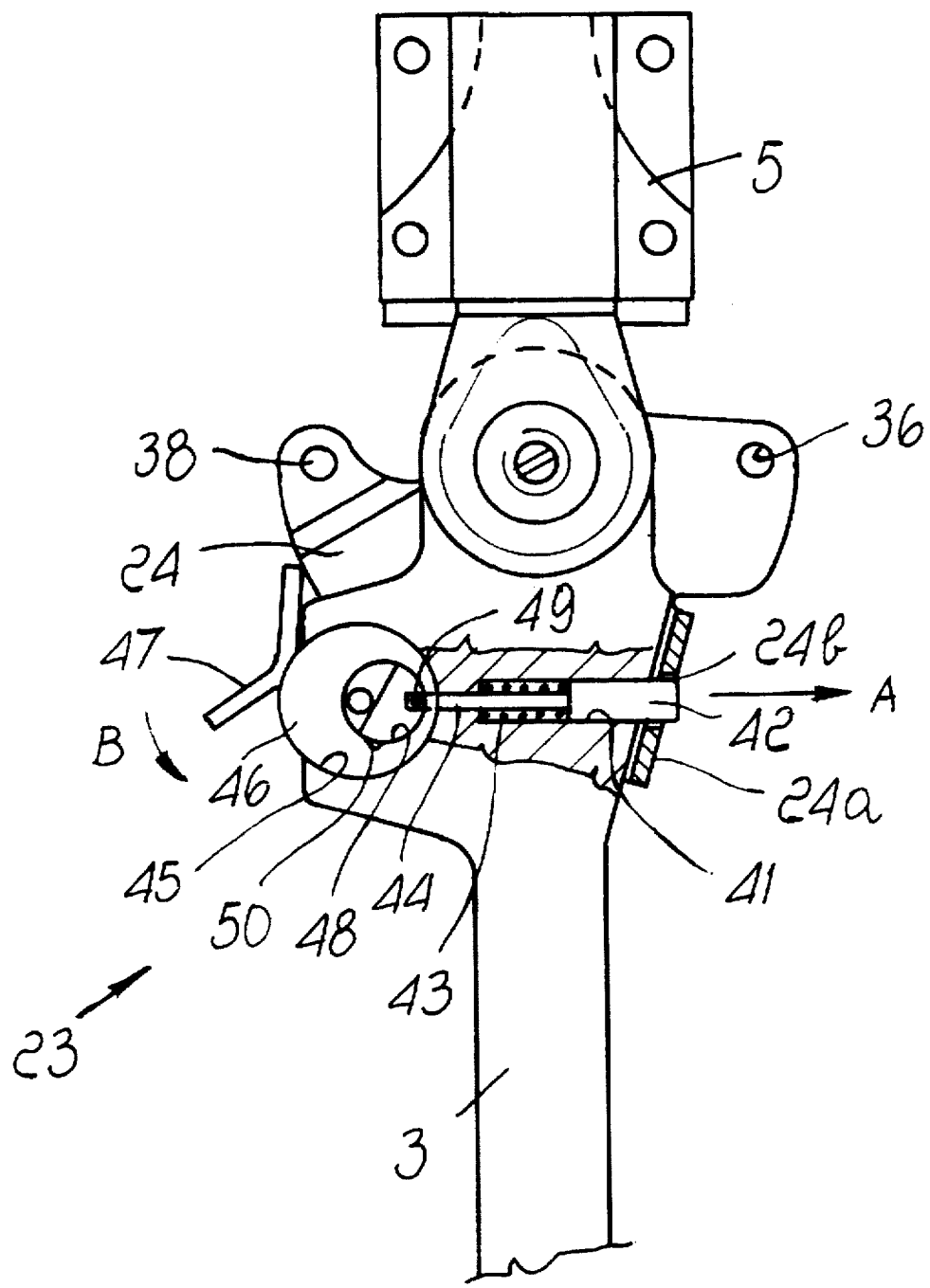
FIG. 5 is a partially sectional side view of the alternative embodiment of the hip locking device.

In the embodiment of FIG. 5, provided for the hip locking device 23, a hole 24b is formed in the contoured stroke limiting lug 24a of the flat element 24: the arm 3 is crossed by a longitudinal hole 41 for the sliding of a pin 42 which, in the hip locking configuration, is pushed by a helical compression spring 43 in the direction of the arrow A, with its end inserted in the hole 24b, and continues with a thin stem 44; a seat 45 is formed in a front position in the arm 3, covers approximately 270°, and affects the passage hole of the thin stem 44; a disk 46 is rotatably mounted in the seat 45, and a shaped trigger 47 is welded to said disk; an eccentric hole 48 is formed in the disk and is connected to a perimetric slit, through which the thin stem 44 can pass: a diametrical dowel 49 is inserted at the end of the thin stem 44 and engages against the profile of the eccentric element 48; one or two stroke limiting notches 50 for the dowel 49 are formed in the profile of the eccentric element 48.

Starting from the locked configuration shown in FIG. 5, with the pin 42 inserted in the hole 24b, the actuation of the trigger in the direction of the arrow B causes the traction of the thin stem 44 under the action of the eccentric element 48 and accordingly causes the extraction of the end of the pin 42 from the hole 24b and the release of the hip joint.

Figure 6:
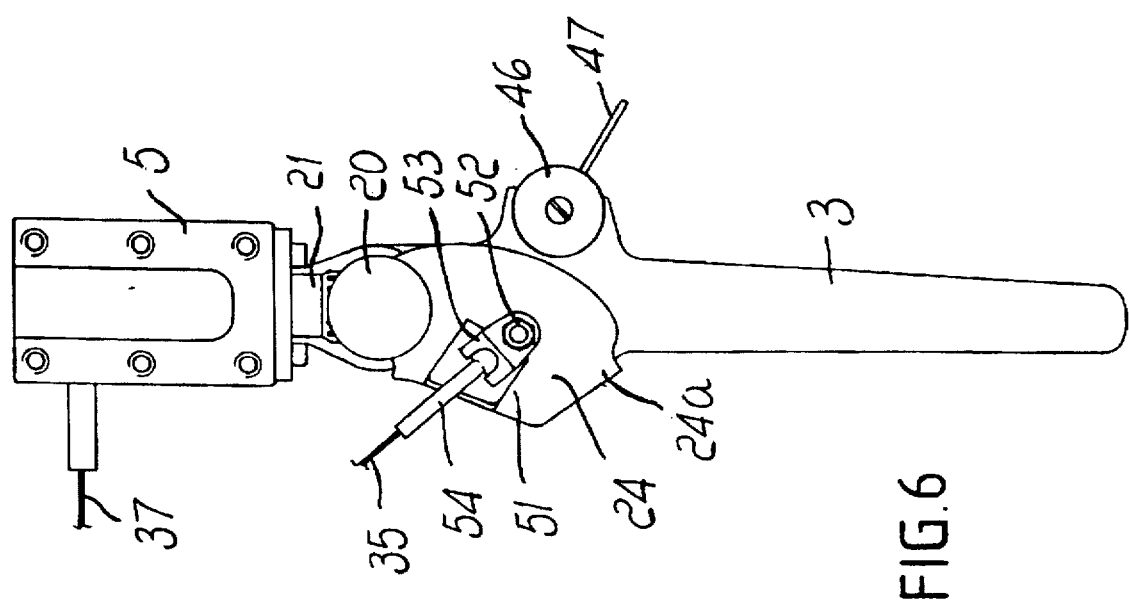
FIG. 6 is a front view of the joint, from the inside, in a preferred embodiment that is a combination of those shown in FIGS. 4 and 5.

In the embodiment shown in FIGS. 6 and 7, the ends of the second cable 37 are coupled to eccentric elements 39 of disks 40 that are fixed to the top of the shafts 10: the hip locking device 23 is provided in a manner that is substantially identical to the one shown in FIG. 5 (pin 42, contoured trigger 47, disk 46, and so forth); the flat element 24, to which the toothed sprocket 20 is rigidly coupled, is arc-shaped; a U-bolt 53 is articulated to said flat element at a recess 51 by means of a bolt 52; said U-bolt oscillatably supports the end of a T-shaped lug 54 for fixing the first cable 35.

It is noted that in the hip joint according to the invention, the couplings of the toothed sprockets 20 to the toothed profiles 21 cause a two-way dependence between the flexion movements and the torsion movements of each arm with respect to the corresponding bushing: when the arm tends to move forwards with respect to the pelvis, an outward torsion is produced; vice versa, when the arm tends to move backwards with respect to the pelvis, an inward torsion is generated.

In practice, considering for the sake of simplicity one side of the pelvic attachment, the arm 3 undergoes a flexion movement with respect to the respective shaft 10, that is a movement in a plane coincident with the axis of the shaft (in other words, a movement around pivot 17), the sprocket element 20, which is rigidly connected to the arm 3, engages with the fixed toothed profile 21 (rigidly connected to the bushing 6). Thus, the flexion movement of the arm is matched by a correspondent torsion movement of the shaft 10 within the bushing 6 and in a plane which is perpendicular to the plane in which the flexion movement is carried out.

The connections due to the sheathed cables coordinate the movements of the right side of the patient with respect to those of the left side, so that the extension movements of one side are matched by the flexion movements of the other side with the respective opposite torsions.

It is thus evident that the invention achieves the intended aim and objects.

The invention thus conceived is susceptible of numerous modifications and variations, all of which are within the scope of the inventive concept.

Furthermore, all the details may be replaced with other technically equivalent ones.

In practice, the materials employed, as well as the shapes and the dimensions, may be any according to the requirements without thereby abandoning the scope of the protection of the appended claims.

What is claimed is:

1. An orthopedic orthesis with left and right hip joints rigidly coupleable to thigh-leg-foot braces for containing and fixing the legs of a patient, the joint comprising:

a pelvic attachment being rigidly coupleable to the pelvic area of the patient;

left and right lateral arms being symmetrically articulated to said pelvic attachment;

a hip locking device provided at each of said arms at a region below the articulation of each arm to the pelvic attachment, said hip locking device being manually disengageable to allow the patient sit;

a couple of bushings, each of said bushings being fixed laterally to a respective side of said pelvic attachment the axis of each bushing being vertical;

left and right shafts, each articulated to one of said bushings so as to be rotatable, said arms being each articulated about a horizontal axis to a respective one of said shafts in a downward region thereof, the axis of said shafts being the same as the axis of said bushings;

kinematic means for kinematically connecting each of said arms to the respective bushing, said kinematic means each comprising a sprocket rigidly coupled to a respective one of said arms, and a fixed toothed profile rigidly coupled to an element fixed to said bushing in a downward region thereof, said sprocket meshing with said toothed profile, each torsion of each of said shafts with respect to the respective bushing being matched by a flexion movement, in a plane coincident with the axis of each shaft, of the respective arm with respect to the shaft so as to create a dependence between a flexion movement and a torsion movement of each arm and shaft with respect to the corresponding bushing; and motion transmission elements for complementary coordinating movements from one of said arms to another, the extension movements of one side being matched by flexion movements of the other side with the respective opposite torsions.

2. The orthesis according to claim 1, wherein said motion transmission elements comprise two sheathed cables having cables slidingly movable in respective sheats, in which ends of the sheats are to be connected to lateral regions of the trunk of a patient, whereas the respective ends of a first and second sliding cables are coupled to a flat element connectable to said arm, said sprocket being connected to said flat element.

3. The orthesis according to claim 2, wherein the ends of each of said second sliding cables are each connected to a respective eccentric element of a disk fixed to the respective shaft at a top portion of said shaft.

4. The orthesis according to claim 2, wherein said flat element is rotatably mounted about a rotation pivot of said arm and is provided with at least one eccentric hole for engaging an end of at least one cable, said hip locking device being arranged between said flat element and the arm.

5. The orthesis according to claim 4, wherein said hip locking device comprises a pin slideably mounted in a hole defined in said arm, said pin being pushed by elastic means, a first end of said pin entering a hole defined in said flat element and a second end of said pin being actuated by a trigger, a cam profile being provided on said arm to facilitate the actuation of said trigger.

* * * * *